(12) United States Patent
Mulholland et al.

(10) Patent No.: US 8,292,852 B2
(45) Date of Patent: Oct. 23, 2012

(54) CATHETER INTRODUCER

(75) Inventors: Patrick Mulholland, Mullingar (IE); David Taylor, Boyle (IE)

(73) Assignee: Vistamed R & D Ltd. (IE)

( * ) Notice: Subject to any disclaimer, the term of this patent is extended or adjusted under 35 U.S.C. 154(b) by 106 days.

(21) Appl. No.: 12/699,608

(22) Filed: Feb. 3, 2010

(65) Prior Publication Data
US 2010/0204654 A1 Aug. 12, 2010

(30) Foreign Application Priority Data

Feb. 6, 2009 (EP) ..................................... 09001699

(51) Int. Cl.
*A61M 5/178* (2006.01)
(52) U.S. Cl. .................................. 604/164.08
(58) Field of Classification Search .............. 604/164.08
See application file for complete search history.

(56) References Cited

U.S. PATENT DOCUMENTS

| | | | |
|---|---|---|---|
| 5,300,045 A | 4/1994 | Plassche, Jr. | |
| 5,344,408 A | 9/1994 | Partika | |
| 6,117,108 A | 9/2000 | Woehr et al. | |
| 6,287,278 B1 | 9/2001 | Woehr et al. | |
| 6,645,178 B1 | 11/2003 | Junker | |
| 6,749,588 B1 | 6/2004 | Howell et al. | |
| 2004/0052296 A1 | 3/2004 | Kuball et al. | |
| 2008/0147003 A1 | 6/2008 | Menzi | |
| 2009/0299291 A1* | 12/2009 | Baid ........................ | 604/164.08 |

FOREIGN PATENT DOCUMENTS

| | | |
|---|---|---|
| DE | 20218551 U1 | 5/2004 |
| EP | 0456694 B1 | 10/1995 |
| EP | 0554841 B1 | 11/1996 |
| EP | 1604700 A1 | 12/2005 |
| EP | 1731192 A2 | 12/2006 |
| EP | 1752188 A | 2/2007 |
| WO | 9222344 A | 12/1992 |
| WO | 9305840 A | 4/1993 |
| WO | 0123029 A1 | 4/2001 |
| WO | 02087672 A1 | 11/2002 |
| WO | 03011381 A | 2/2003 |
| WO | 2008021132 A1 | 2/2008 |

OTHER PUBLICATIONS

European Search Report dated Aug. 28, 2009.
Official Communication from the European Patent Office corresponding to Application No. 09 001 699.9-1526 mailed Nov. 10, 2011.

* cited by examiner

*Primary Examiner* — Nicholas Lucchesi
*Assistant Examiner* — Jason Flick
(74) *Attorney, Agent, or Firm* — Amster, Rothstein & Ebenstein LLP

(57) ABSTRACT

The invention relates to a catheter introducer comprising: a tube-like introducer sheath; an introducer hub having a distal section and a proximal section, wherein the distal section is joined to the proximal end of the introducer sheath and the proximal section defines a chamber; a needle extending through the introducer hub and the introducer sheath and having opposite proximal and distal ends, the distal end forming a needle tip; a needle hub attached to the proximal end of the needle; a needle safety device slidably arranged on the needle, wherein the needle safety device is retained in the chamber of the introducer hub when the needle extends through the introducer hub and the introducer sheath, and removable from the introducer hub once the needle tip is received in the needle safety device upon withdrawal of the needle from the introducer sheath.

19 Claims, 6 Drawing Sheets

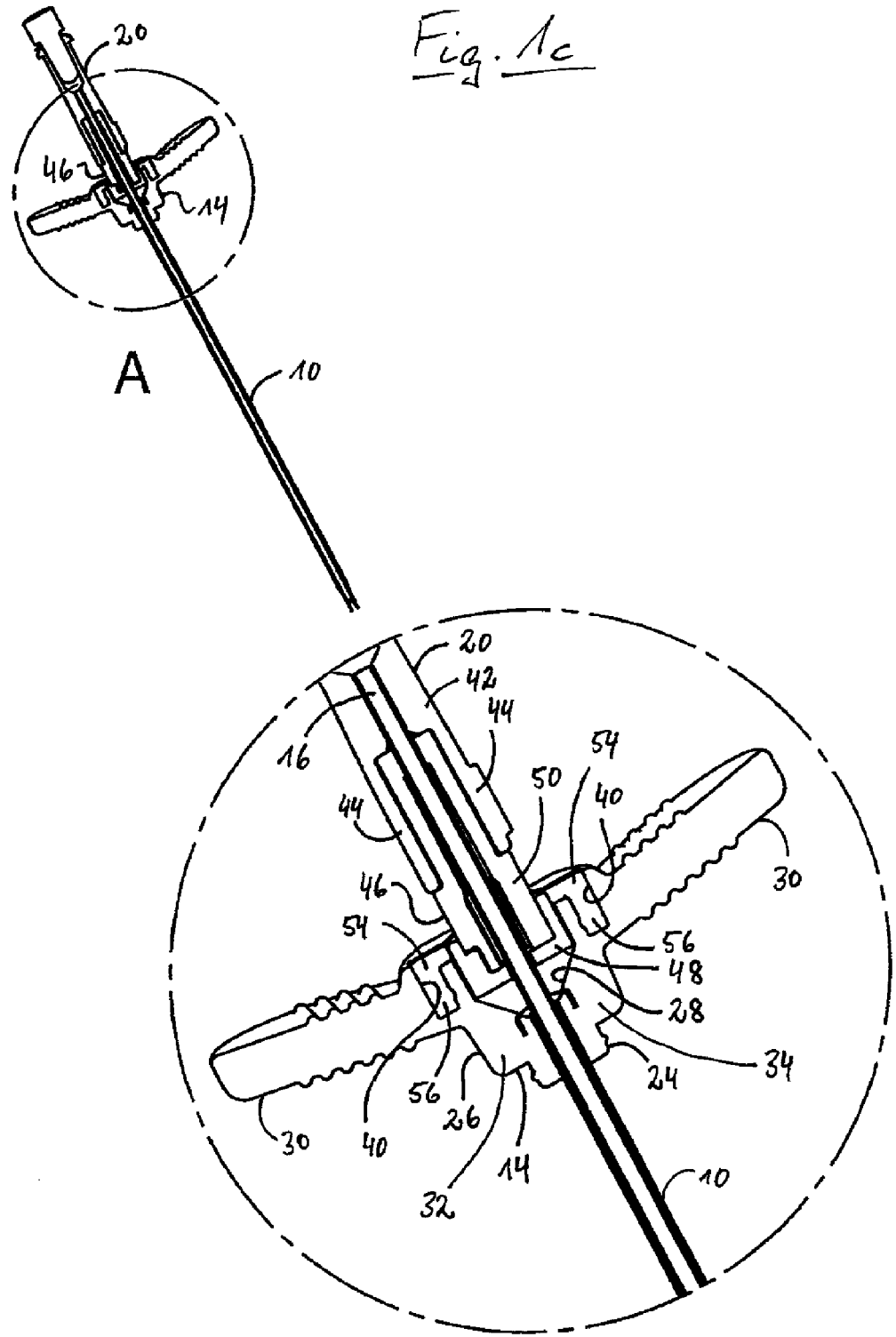

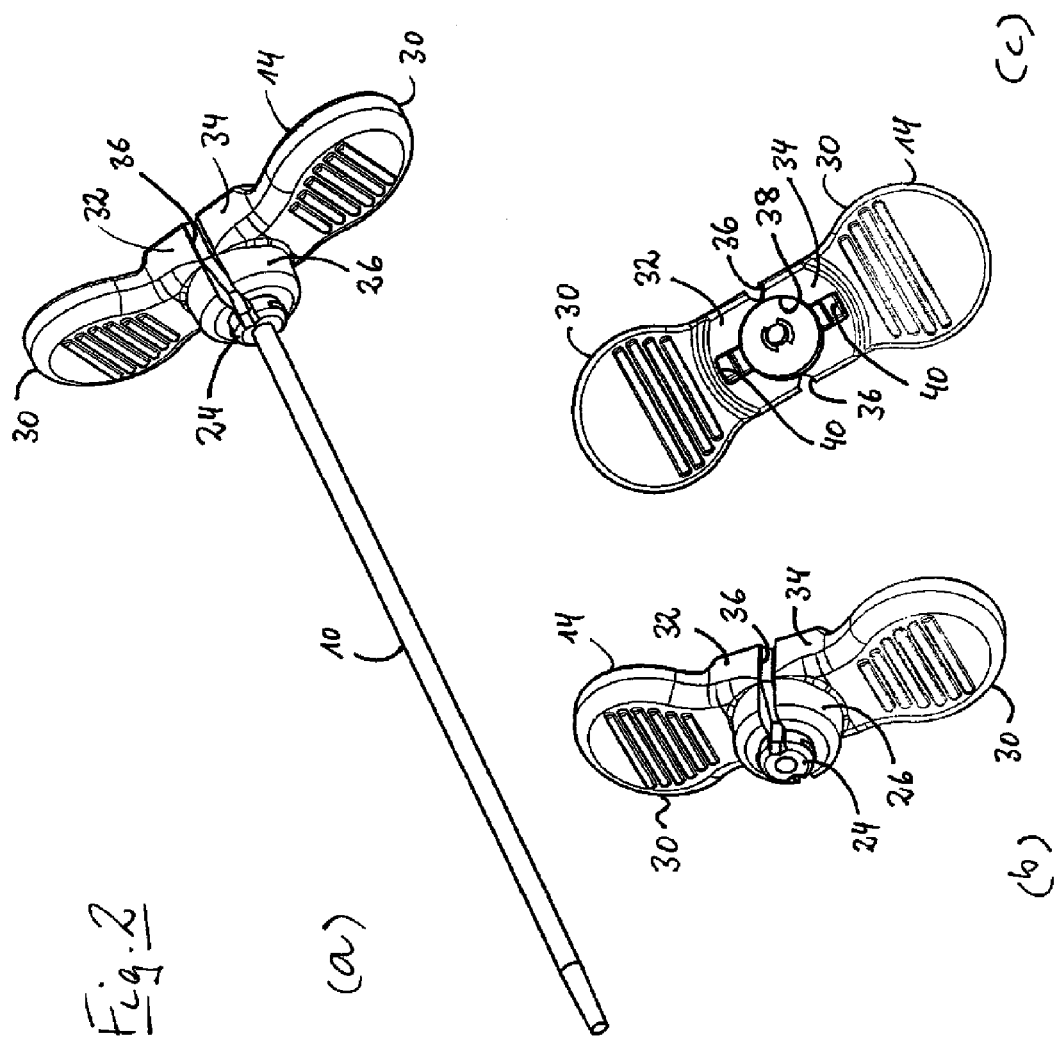

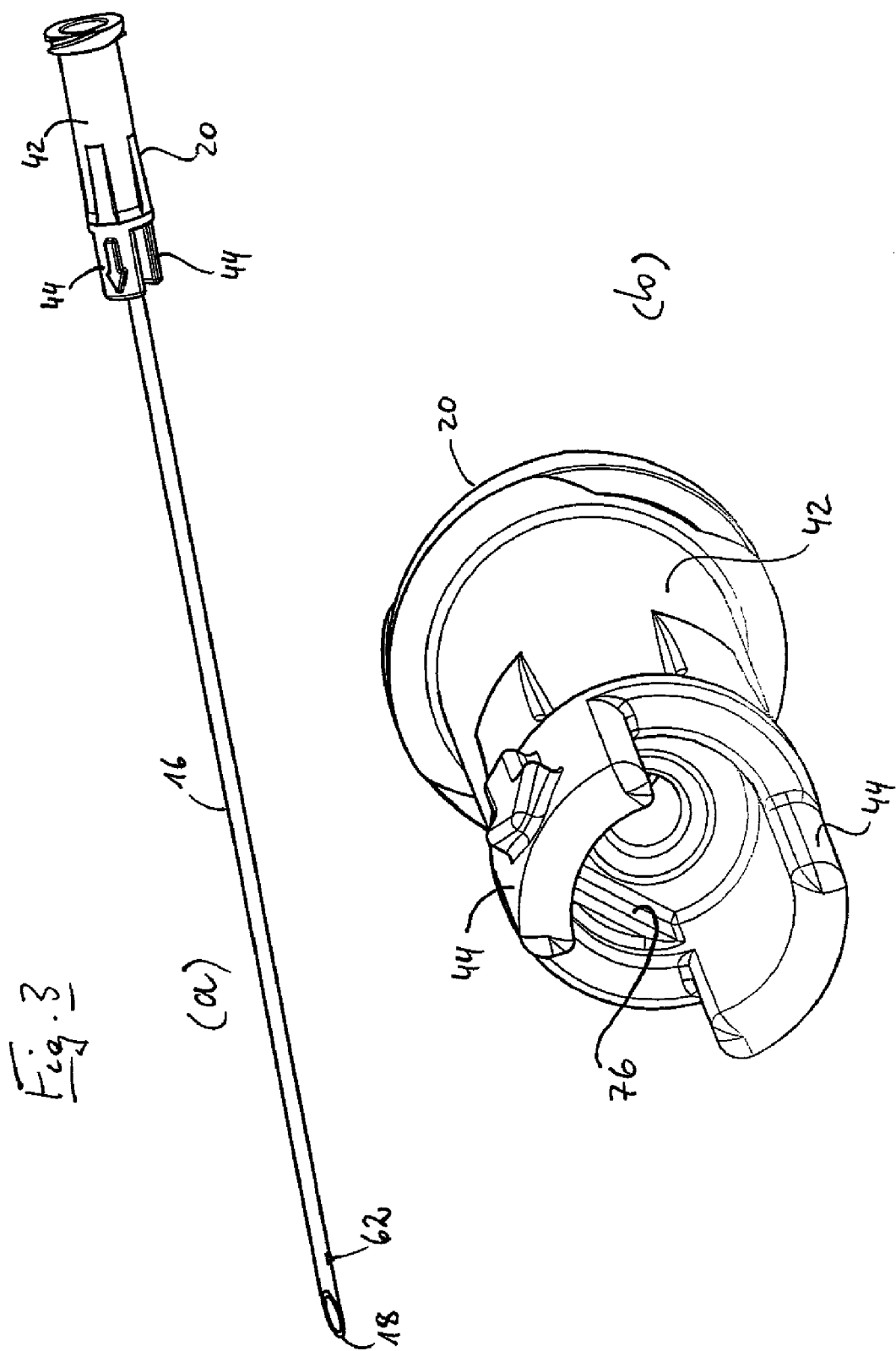

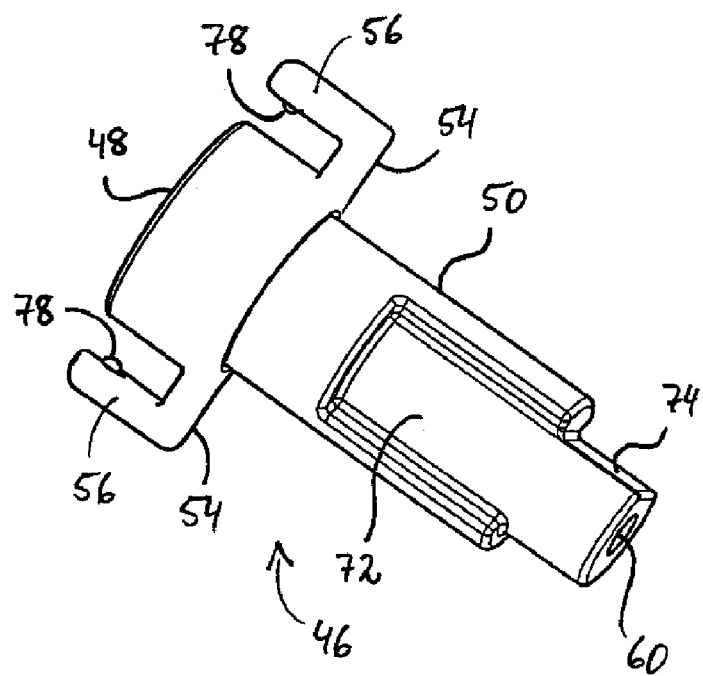
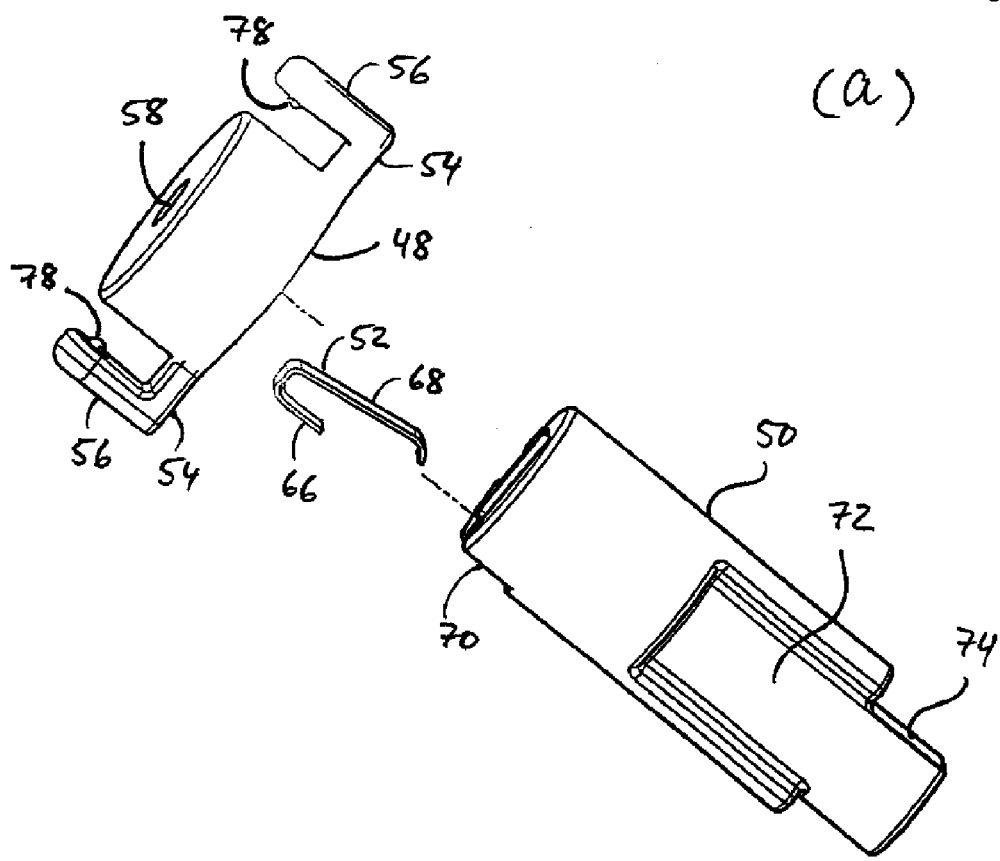
Fig. 4
(a)
(b)

Fig. 5
(a) 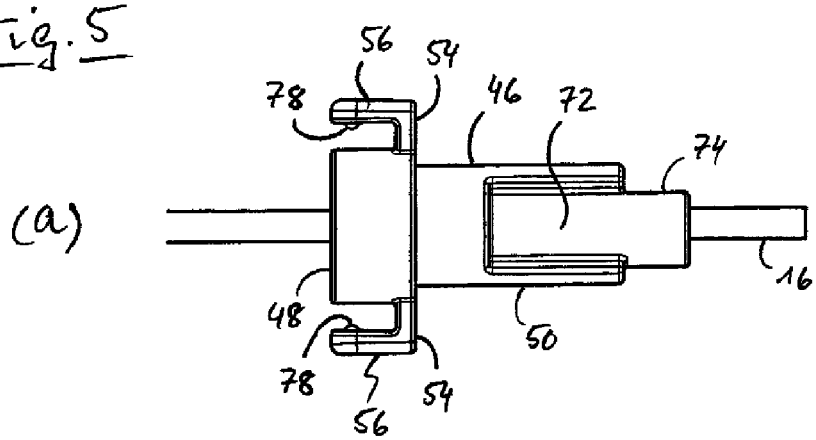
(b) 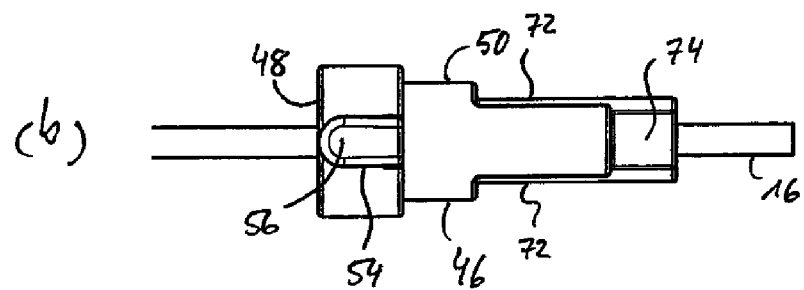
(c) 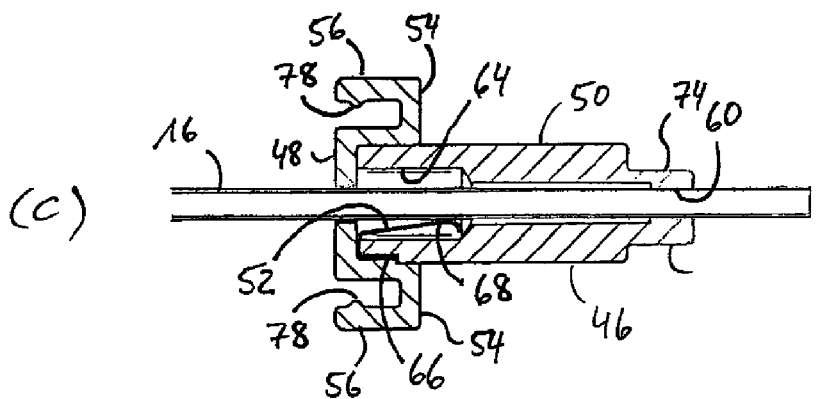

CATHETER INTRODUCER

The present invention relates to a catheter introducer, in particular an over-the-needle peel-away catheter introducer, comprising a tube-like introducer sheath; an introducer hub having a distal section and a proximal section, wherein the distal section is joined to a proximal end of the introducer sheath and the proximal section defines a chamber; a needle extending through the introducer hub and the introducer sheath and having opposite proximal and distal ends, wherein the distal end forms a needle tip; and a needle hub attached to the proximal end of the needle.

As used herein, the term proximal refers to a location on the device closest to, for example, a clinician using the device. Conversely, the term distal refers to a location on the device farthest from the clinician, such as the distal needle tip to be inserted into a patient's vein.

A catheter introducer of the above kind is generally known and, for example, used to facilitate insertion and placement of a catheter or another medical device into a patient's vasculature or into a patient's muscular tissue. A catheter of this kind can, for instance, be used for pain management in connection with knee or hip replacements or other applications such as caesarean sections.

A conventional peel-away catheter introducer, which is also referred to as a peelable, splittable or tear-away catheter introducer comprises a pair of wings extending transversely from the introducer hub.

When using the peel-away catheter introducer a clinician grabs the needle hub along with the introducer hub and inserts the distal end portion of the needle at a selected site into a patient's skin. The clinician advances the device, for example, until venipuncture has been confirmed, e.g when blood enters a flashback chamber formed in the needle hub. After venipuncture has been confirmed, the clinician advances the distal end portion of the introducer sheath into the patient's vein and withdraws the needle. With the introducer sheath properly placed, the clinician can then insert a medical device, such as a catheter, into the proximal opening of the introducer sheath via the introducer hub and advance the medical device through the introducer sheath until it is properly placed in the patient's vasculature.

After placement of the medical device the clinician withdraws the introducer sheath out of the venipuncture site. The clinician then splits the introducer hub and introducer sheath into two respective separate halves by a combination of twisting and/or pulling apart of the wings along tear lines provided in the introducer hub and introducer sheath until the two halves of the introducer hub and introducer sheath split apart. The clinician can thus remove the introducer hub and introducer sheath while the catheter inserted into the patient's vein remains in place.

Due to the increasing incidence of blood born pathogens such as human immunodeficiency virus (HIV), hepatitis B virus (HBV) and hepatitis C virus (HCV) there is a need to protect clinicians or other medical professionals or personnel handling catheter introducers from accidental contact with the sharp needle tip after withdrawal of the needle from the introducer sheath and introducer hub.

It is an object of the invention to provide a catheter introducer which provides reliable protection against accidental pricking by the needle once the needle has been withdrawn from the introducer sheath and introducer hub.

This object is satisfied by a catheter introducer having the features of claim 1.

The catheter introducer of the invention comprises a tube-like introducer sheath; an introducer hub having a distal section and a proximal section, wherein the distal section is joined to a proximal end of the introducer sheath and the proximal section defines a chamber; a needle extending through the introducer hub and the introducer sheath and having opposite proximal and distal ends, wherein the distal end forms a needle tip; a needle hub attached to the proximal end of the needle; and a needle safety device slidably arranged on the needle, wherein the needle safety device is retained in the chamber of the introducer hub when the needle extends through the introducer hub and the introducer sheath, and removable from the introducer hub once the needle tip is received in the needle safety device upon withdrawal of the needle from the introducer sheath.

The needle safety device is operative as a guard for the needle tip by automatically covering the needle tip during withdrawal of the needle from the introducer sheath. The needle safety device thereby serves to prevent accidental pricking of, for example, a clinician by the needle tip after removal of the needle from a patient. Hence, the needle can be safely disposed of after use.

According to an advantageous embodiment of the catheter introducer of the invention, a distal part of the needle safety device is received in a positive fit in the chamber of the introducer hub. Thereby a secure seat of the needle safety device in the introducer hub is achieved. Preferably, the distal part of the needle safety device is generally completely received in the chamber of the introducer hub.

According to a further embodiment, the needle safety device comprises two generally L-shaped extensions formed on opposite sides of the needle safety device, preferably in a distal region thereof. Each L-shaped extension may have an axial section extending generally in an axial direction at a distance from a main body of the distal part of the needle safety device. As used herein, the axial direction is defined by the longitudinal axis of the needle extending through the needle safety device.

The proximal section of the introducer hub may comprise two receptacles which are formed on opposite sides of the chamber, in particular in different portions of the introducer hub which define two separate halves after tearing the introducer hub apart. Preferably, the receptacles of the introducer hub are adapted to receive the axial sections of the generally L-shaped extensions of the needle safety device, in particular in a positive fit, thereby guaranteeing a correct rotational positioning of the needle safety device relative to the introducer hub and a secure seat of the needle safety device in the introducer hub.

Due to the axial sections of the generally L-shaped extensions of the needle safety device engaging in the receptacles of the introducer hub, the needle safety device helps to prevent the two halves of the introducer hub from being accidentally torn apart, thereby contributing to the reliable functioning of the catheter introducer. Hence, the needle safety device performs a double function, specifically a locking function and a guarding function, by interlocking the two halves of the introducer hub as long as it is engaged with the introducer hub and by guarding the needle tip after withdrawal of the needle from the introducer sheath.

According to a further embodiment, locking means are provided to hold the axial sections of the generally L-shaped extensions of the needle safety device in the receptacles. The locking means help to secure the needle safety device in the introducer hub as long as the needle has not been fully withdrawn from the introducer sheath and the needle tip has not entered the needle safety device. Hence, the locking means ensures that the needle moves relative to the needle safety device until the needle tip is safely received in the needle safety device and thus adds to a correct functioning of the needle safety device.

Preferably, the locking means operating between the introducer hub and the needle safety device comprise a locking protrusion at the respective one part and a corresponding locking depression at the respective other part. For instance, respective locking protrusions may be provided in the region of distal ends of the generally L-shaped extensions of the needle safety device, whereas corresponding depressions may be provided in walls defining the receptacles in the introducer hub.

According to a further embodiment, a distal part of the needle safety device has a generally cup-like shape. A proximal part of the needle safety device may be of generally tubular shape. These shapes help to prevent the needle tip received in the needle safety device from protruding sideways out of the needle safety device, thereby increasing the protective function of the needle safety device.

Advantageously, the proximal part of the needle safety device is partly received in the distal part of the needle safety device. In order to guarantee a secure seat of the tubular proximal part in the cup-like distal part, preferably, an outer diameter of the tubular proximal part is adapted to an inner diameter of the cup-like distal part. The tubular proximal part and the cup-like distal part may be connected with each other, preferably permanently, for example, by an adhesive and/or a welded connection.

According to a further embodiment, the distal part and/or the proximal part of the needle safety device each is made of a plastic material. This choice of material allows for easy and low cost manufacturing of the needle safety device. However, it is generally also possible to make the distal part and/or the proximal part of the needle safety device from another material, e.g. a metal material.

According to a further embodiment, the needle safety device comprises a spring clip, preferably a metal clip, which prevents the needle tip from protruding from the needle safety device at the distal end thereof once the needle tip has entered the needle safety device.

The spring clip may have a generally V-like form. In particular, the spring clip may comprise a first leg and a second leg the free ends of which generally extend towards the proximal end of the needle safety device.

Preferably, a first leg of the spring clip is fixedly arranged between the distal part and the proximal part of the needle safety device and/or a second leg of the spring clip extends diagonally across an inner chamber formed in the distal region of the proximal part the needle safety device when disengaged from the needle, thereby blocking the needle tip from protruding from the needle safety device at the distal end thereof. In other words, the spring clip is arranged such that it is compressed by the needle while the needle fully extends through the needle safety device and relaxes when disengaged from the needle, with the second leg of the spring clip adopting its diagonal "blocking" position. Due to its elastic properties the spring clip ensures a reliable guarding of the needle tip upon withdrawal of the needle from the introducer sheath even after a longer shelf time, thereby continuously ensuring a correct functioning of the needle safety device.

According to a further embodiment, guiding means are provided to ensure a correct rotational positioning of the needle hub in the assembled state of the catheter introducer. Preferably, the guiding means are provided on the needle hub and on the needle safety device. The needle hub can thus be correctly positioned with respect to the introducer hub via the needle safety device which in turn is correctly positioned with respect to the introducer hub by means of its L-shaped extensions received in the receptacles of the introducer hub.

For example, the guiding means may comprise two channels extending in an axial direction on opposite sides of the proximal part of the needle safety device, and two guiding protrusions extending in an axial direction from the needle hub and adapted to be received in the channels of the needle safety device, preferably in a positive fit.

According to a further embodiment, the needle extends through an axial bore in the proximal part of the needle safety device, wherein the cross section of the bore is adapted to the main profile of the needle. Preferably, the needle has an enlargement near the needle tip, which renders the outer diameter of the needle, seen in at least one direction, greater than the diameter of the bore. The enlargement prevents the needle safety device from sliding off the needle when the needle tip is received in the inner chamber of the proximal part of the needle safety device, thereby further improving the protective function of the needle safety device.

Further subject matter of the invention is a needle safety device for guarding the tip of a needle of a medical apparatus, for example, a catheter introducer of the above described type or an intravenous catheter apparatus, which comprises a distal part and a proximal part as well as two generally L-shaped extensions formed on opposite sides of a main body of the distal part (claim 14). Apart from that, the needle safety device may be configured similar to the needle safety device of the above described catheter introducer.

Preferred embodiments of the invention are described in the following description and in the accompanying drawings, wherein:

FIG. 2 shows (*a*) a perspective view of an introducer hub of the catheter introducer of FIG. 1 with an introducer sheath attached thereto, (*b*) a view of the distal side of the introducer hub without the introducer sheath, and (*c*) a view of the proximal side of the introducer hub without the introducer sheath;

FIG. 3 shows perspective views of a needle hub of the catheter introducer of FIG. 1 (*a*) with a needle attached thereto and (*b*) without the needle;

FIG. 4 shows perspective views of a needle safety device of a catheter introducer of FIG. 1 (*a*) in an assembled state and (*b*) in a disassembled state;

FIG. 5 shows (*a*) a first side view, (*b*) a second side view and (*c*) a longitudinal sectional view of the needle safety device of FIG. 4 with a needle extending completely there through.

Figure 1A:
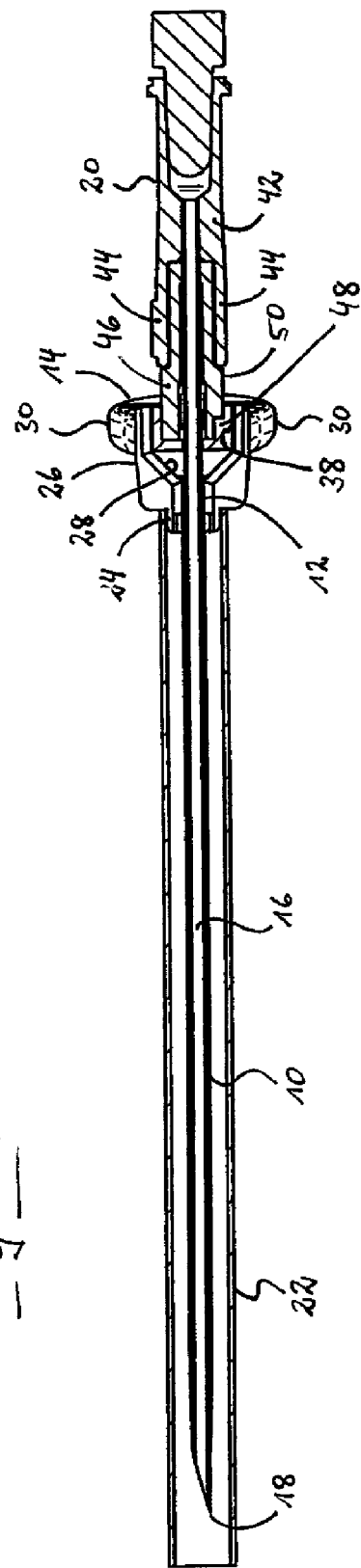
FIG. 1 shows (*a*) a first longitudinal sectional view, (*b*) a side view and (*c*) a second longitudinal sectional view of a catheter introducer in accordance with the invention.
Figure 1B:
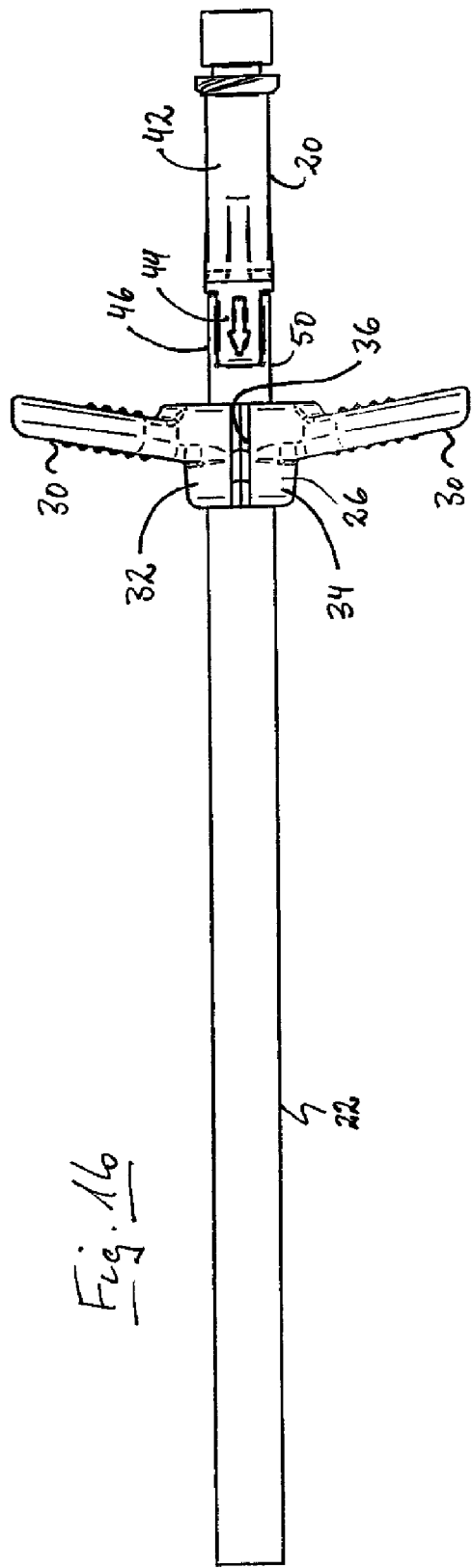

FIG. 1 shows an over-the-needle peal-away catheter introducer of the invention. The catheter introducer comprises a tube-like introducer sheath 10 having a proximal end region 12 that is joined to an introducer hub 14.

Furthermore, the catheter introducer comprises a needle 16 having a distal end that forms a needle tip 18 and a proximal end that is attached to a needle hub 20. Prior to use of the catheter introducer, the needle 16 extends all the way through the introducer hub 14 and the introducer sheath 10 and the needle tip 18 protrudes beyond a distal end of the introducer sheath 10.

In order to prevent accidental pricking by the needle tip 18 prior to use of the catheter introducer, an elongate protective tube 22 is mounted to the introducer hub 14, which covers the length of the introducer sheath 10 and also the needle tip 18 protruding therefrom.

The introducer hub 14 includes a distal section 24 and a proximal section 26 (FIG. 1a). The distal section 24 has smaller inner and outer diameters than the proximal section 26 and is joined to the proximal end region 12 of the introducer sheath 10.

In the transition region between the distal section 24 and the proximal section 26 a funnel-like structure 28 is formed in the introducer hub 14, which helps to facilitate the introducing of a medical device, for example a catheter, into the introducer sheath 10 after the introducer sheath 10 has been inserted into the vein of a patient. Furthermore, two wings 30 extend transversely from the proximal section 26 of the introducer hub 14.

As can be seen in FIG. 2, both the distal section 24 and the proximal section 26 of the introducer hub 14 are formed from pairs of opposite axially extending generally semi-tubular sections, which define first and second halves 32, 34 of the introducer hub 14. Prior to use, the first and second halves of the introducer hub 14 are connected to each other at least in the region of the distal section 24 of the introducer hub 14.

Once a medical device, such as a catheter, has been introduced through the introducer sheath 10 into a patient's vein, the person handling the catheter introducer, for example a clinician, withdraws the introducer sheath 10 from the venipuncture site. By a combination of twisting and/or pulling apart of the wings 30 the clinician then splits the introducer hub 14 into its two separate halves 32, 34, thereby also tearing the introducer sheath 10, such that the introducer hub 14 and the introducer sheath 10 can be removed from the catheter. In order to facilitate the breaking of the introducer hub 14 into its two halves, axially extending grooves 36 are provided on opposite sides of the introducer hub 14, which function as tear lines. Similarly, corresponding tear lines (not shown) may be provided on the introducer sheath 10.

The proximal section 26 of the introducer hub 14 defines a cylindrical chamber 38 which is arranged concentrically with the middle axis of the introducer hub 14 and which is open towards the proximal side of the introducer hub 14 (FIG. 2c). Two receptacles 40 are formed on opposite sides of the chamber 38. The receptacles 40 have a generally rectangular cross-section and extend axially into the introducer hub 14 from the proximal side thereof.

As can be seen in FIG. 3, the needle hub 16 comprises a main body 42 and two opposite tube sections 44 which extend axially from a distal end of the main body 42.

Referring again to FIG. 1, a needle safety device 46 is slidably arranged on the needle 16 and arranged between the introducer hub 14 and the needle hub 20. The needle safety device 46 will now be discussed in more detail with reference to FIGS. 4 to 6.

The needle safety device 46 comprises a distal part 48, a proximal part 50 and a spring clip 52.

In the present embodiment both the distal part 48 and the proximal part 50 of the needle safety device 46 are made from a plastic material, whereas the spring clip 52 is made of a metal material, for example spring steel.

The distal part 48 comprises a main body 53 of generally cup-like shape, which defines an inner diameter and an outer diameter. Two generally L-shaped extensions 54 are formed on opposite sides of the main body 53 of the distal part 48. Each L-shaped extension 54 has an axial section 56 extending generally axially at a distance from the main body 53 and having a generally rectangular cross-section which is adapted to the cross-section of the receptacles 40.

The proximal part 50 of the needle safety device 46 is of generally tubular shape, wherein a distal portion of the proximal part 50 has an outer diameter that is adapted to the inner diameter of the cup-like main body 53 of the distal part 48.

In the assembled state of the needle safety device 46 the distal part 48 is fitted onto the distal region of the proximal part 50 and permanently fixed thereto, for example, by an adhesive or by a welded connection.

The distal part 48 and the proximal part 50 of the needle safety device 46 each define a bore 58 and 60, respectively, for receiving the needle 16. The diameter of the bore 58 in the distal part 48 is adapted to allow an enlargement 62 arranged in the distal end region of the needle 16 (cf. FIG. 3a) to pass, whereas the enlargement 62 of the needle 16 cannot pass the bore 60 of the proximal part 50, thereby preventing the needle safety device 46 from sliding off the distal end of the needle 16. The enlargement 62 of the needle 16 may, for instance, be formed by a crimping process.

Figure 6:
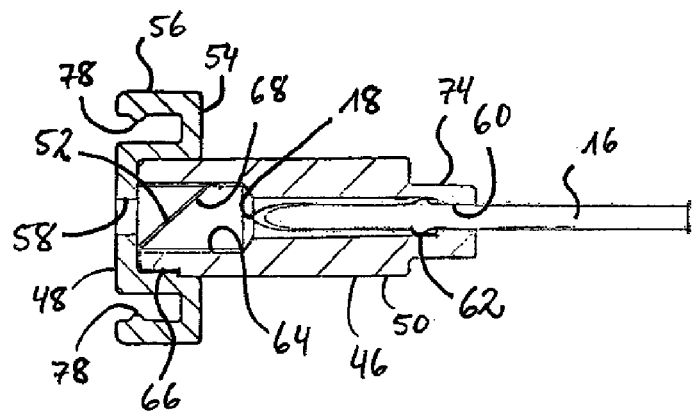
FIG. 6 shows a longitudinal sectional view of the needle safety device of FIG. 5 with the tip of the needle trapped therein.

As illustrated in FIGS. 5c and 6, the proximal part 50 of the needle safety device 46 defines an inner chamber 64 in its distal region, which has a diameter greater than the diameter of the bore 60.

The spring clip 52 has a generally V-like form and comprises a shorter first leg 66 and a longer second leg 68. The free ends of the legs 66, 68 generally extend towards the proximal end of the needle safety device 46.

In the assembled state of the needle safety device 46, the shorter first leg 66 of the spring clip 52 is arranged—as seen in the radial direction—between the proximal part 50 and the distal part 48. In order to provide room for the first leg 66 and to ensure a correct positioning of the spring clip 52, the proximal part 50 is provided with a flat surface portion 70 in its distal region (FIGS. 4b, 5c and 6).

When the spring clip 52 is disengaged from the needle 16, its longer second leg 68 extends diagonally across the inner chamber 64 of the proximal part 50, such that in the region of its free end the second leg 68 abuts against a wall portion of the proximal part 50 opposite from the first leg 66 (FIG. 6). This state of the spring clip 52 is referred to as a relaxed state of the spring clip 52.

In the assembled state of the catheter introducer and prior to use, the needle 16 extends completely through the needle safety device 46, thereby deflecting the second leg 68 of the spring clip 52 towards the first leg 68 against a restoring force of the spring clip 52, as shown in FIG. 5c. This state of the spring clip 52 is referred to as the compressed state of the spring clip 52.

As can be taken from FIG. 4, two guiding channels 72 are formed on opposite sides of the proximal part 50 in a proximal region thereof. The guiding channels 72 extend in the axial direction and are adapted to receive the axial tube sections 44 of the needle hub 20 in a positive fit.

In addition, a flat surface portion 74 is provided in the proximal end region of the proximal part 50 of the needle safety device 46, wherein the flat surface portion 74 is arranged in a rotational angle of 90° with respect to the guiding channels 72 (FIGS. 4 and 5). A corresponding flat surface portion 76 is provided at the inner surface of the needle hub 20 (FIG. 3).

The guiding channels 72 of the proximal part 50 and the axial tube sections 44 of the needle hub 20 together with the flat surface portions 74, 76 of the proximal part 50 of the needle safety device 46 and the needle hub 20, respectively, ensure a correct rotational positioning of the needle hub 20 with respect to the needle safety device 46 in the assembled state of the catheter introducer.

In the assembled state of the catheter introducer, as shown in FIG. 1, the introducer hub 14, the needle safety device 46 and the needle hub 20 are pushed together such that the cup-like main body 53 of the distal part 48 is received in the cylindrical chamber 38 of the introducer hub 14 and the axial sections 56 of the L-shaped extensions 54 are received in the receptacles 40 of the introducer hub 14 (FIG. 1c), thereby preventing the two halves 32, 34 of the introducer hub 14 from accidentally being torn apart. At the same time the proximal portion of the proximal part 50 of the needle safety device 46 is received in the needle hub 20.

In order to secure the distal part 48 of the needle safety device 46 in the introducer hub 14, locking protrusions 78 are formed at the inner surfaces of the axial sections 56 of the L-shaped extensions 54 (FIG. 4). The locking protrusions 78 are adapted to engage with corresponding locking depressions (not shown) formed in the walls that define the receptacles 40. When the needle 16 is withdrawn from the introducer sheath 10, e.g. by pulling on the needle hub 20, the needle safety device 46 is retained in the introducer hub 14 and the needle 16 can freely slide through the needle safety device 46 until the needle tip 18 enters the inner chamber 64 of the proximal part 50 of the needle safety device 46.

As soon as the needle tip 18 has passed the free end of the second leg 68 of the spring clip 52, the spring clip 52 adopts its relaxed state thereby blocking the needle tip 18 from re-exiting the needle safety device 46 via the bore 58 in the distal part 48. Generally at the same time significant further axial movement of the needle 16 with respect to the needle safety device 46 is prevented by the enlargement 62 of the needle 16 abutting against the entry of the bore 60 in the proximal part 50, and the needle safety device 46 can be removed from the introducer hub 14 against the locking force exerted by the locking protrusions 78 engaging the locking depressions. As a result, the needle tip 18 is trapped inside the needle safety device 46 and the needle 16 can be safely disposed of.

REFERENCE NUMERAL LIST 10 introducer sheath
12 proximal end region
14 introducer hub
16 needle
18 needle tip
20 needle hub
22 protective tube
24 distal section
26 proximal section
28 funnel-like structure
30 wing
32 introducer half
34 introducer half
36 groove
38 cylindrical chamber
40 receptacle
42 main body
44 tube section
46 needle safety device
48 distal part
50 proximal part
52 spring clip
53 main body
54 L-shaped extension
56 axial section
58 bore
60 bore
62 enlargement
64 inner chamber
66 first leg
68 second leg
70 flat surface portion
72 guiding channel
74 flat surface portion
76 flat surface portion
78 locking protrusion

The invention claimed is:

1. An over-the-needle peel-away catheter introducer comprising:
   a tube-like introducer sheath (10);
   an introducer hub (14) having a distal section (24) and a proximal section (26), wherein the distal section (24) is joined to the introducer sheath (10) and the proximal section (26) defines a chamber (38);
   a needle (16) extending through the introducer hub (14) and the introducer sheath (10) and having opposite proximal and distal ends, wherein the distal end forms a needle tip (18);
   a needle hub (20) attached to the proximal end of the needle (16); and
   a needle safety device (46) slidably arranged on the needle (16), wherein the needle safety device (46) is retained in the chamber (38) of the introducer hub (14) when the needle (16) extends through the introducer hub (14) and the introducer sheath (10), and removable from the introducer hub (14) once the needle tip (18) is received in the needle safety device (46) upon withdrawal of the needle (16) from the introducer sheath (10), and
   wherein the needle safety device (46) comprises a distal part (48) which has a main body (53) of generally cup like shape; a proximal part (50) which is partly received in the distal part (48) and defines an inner chamber (64); a spring clip (52) having a first leg (66) and a second leg (68), wherein the first leg (66) is fixedly arranged between the distal part (48) and the proximal part (50) and the second leg (68) extends diagonally across the inner chamber (64) when disengaged from the needle (16); and two generally L-shaped extensions (54) formed on opposite sides of the main body (53) of the distal part (48).

2. A catheter introducer in accordance with claim 1, characterized in that the distal part (48) of the needle safety device (46) is received in a positive fit in the chamber (38) of the introducer hub (14).

3. A catheter introducer in accordance with claim 1, characterized in that each L-shaped extension (54) has an axial section (56) extending generally in an axial direction at a distance from the main body (53).

4. A catheter introducer in accordance with claim 1 characterized in that the proximal section (26) of the introducer hub (14) comprises two receptacles (40) formed on opposite sides of the chamber (38) and adapted to receive axial sections (56) of the generally L-shaped extensions (54).

5. A catheter introducer in accordance with claim 4, characterized in that locking means (78) are provided to hold the axial sections (56) in the receptacles (40).

6. A catheter introducer in accordance with claim 1, characterized in that the proximal part (50) of the needle safety device (46) is of generally tubular shape.

7. A catheter introducer in accordance with claim 1, characterized in that the proximal part (50) of the needle safety device (46) is permanently fixed to the distal part (48) of the needle safety device (46).

8. A catheter introducer in accordance with claim 1, characterized in that the spring clip (52) is a metal clip which prevents the needle tip (18) from protruding from the needle safety device (46) at the distal end thereof once the needle tip (18) has entered the needle safety device (46).

9. A catheter introducer in accordance with claim 1, characterized in that the spring clip (52) has a generally V-like form and, wherein the free ends of the first leg (66) and the second leg (68) generally extend towards the proximal end of the needle safety device (46).

10. A catheter introducer in accordance with claim 1, characterized in that guiding means (44, 72, 74, 76) are provided to ensure a correct rotational positioning of the needle hub (20) in the assembled state of the catheter introducer.

11. A catheter introducer in accordance with claim 10, characterized in that the guiding means comprise two channels (72) of the needle safety device (46), which extending in an axial direction on opposite sides of the proximal part (50) and two guiding protrusions (44) of the needle hub (20), which extend in an axial direction from the needle hub (20) and are adapted to be received in the channels (72) of the needle safety device (46).

12. A catheter introducer in accordance with claim 1, characterized in that at least one of the distal part (48) and the proximal part (50) of the needle safety device (46) is made of a plastic material.

13. A needle safety device (46) in accordance with claim 11, characterized in that at least one of the distal part (48) and the proximal part (50) of the needle safety device (46) is made of a plastic material.

14. A needle safety device (46) for guarding the tip (18) of a needle (16) of a medical apparatus, comprising:
a distal part (48) which has a main body (53) of generally cup like shape;
a proximal part (50) which is partly received in the distal part (48) and defines an inner chamber (64);
a spring clip (52) having a first leg (66) and a second leg (68), wherein the first leg (66) is fixedly arranged between the distal part (48) and the proximal part (50) and the second leg (68) extends diagonally across the inner chamber (64) when disengaged from the needle (16); and
two generally L-shaped extensions (54) formed on opposite sides of the main body (53) of the distal part (48).

15. A needle safety device (46) in accordance with claim 14, characterized in that each L-shaped extension (54) has an axial section (56) extending generally in an axial direction at a distance from the main body (53).

16. A needle safety device (46) in accordance with claim 14, characterized in that the proximal part (50) is of generally tubular shape.

17. A needle safety device (46) in accordance with claim 14, characterized in that the proximal part (50) is permanently fixed to the distal part (48).

18. A needle safety device (46) in accordance with claim 14, characterized in that the spring clip (52) is a metal clip which prevents the needle tip (18) from protruding from the needle safety device (46) at the distal end thereof once the needle tip (18) has entered the needle safety device (46).

19. A needle safety device (46) in accordance with claim 14, characterized in that the spring clip (52) has a generally V-like form, wherein the free ends of the first leg (66) and the second leg (68) generally extend towards the proximal end of the needle safety device (46).

* * * * *